United States Patent [19]

Lunstroth

[11] 4,236,405
[45] Dec. 2, 1980

[54] PENDULUM DENSIMETER

[76] Inventor: Klaus Lunstroth, 4746 Pease St., Houston, Tex. 77023

[21] Appl. No.: 404

[22] Filed: Jan. 2, 1979

Related U.S. Application Data

[63] Continuation-in-part of Ser. No. 688,266, May 20, 1976, Pat. No. 4,136,551.

[51] Int. Cl.³ ............................................. G01N 9/10
[52] U.S. Cl. .................................................... 73/32 R
[58] Field of Search ................. 73/32 R, 30, 440, 441, 73/448, 451, 452, 453, 454

[56] References Cited

U.S. PATENT DOCUMENTS

| | | | |
|---|---|---|---|
| 2,072,162 | 3/1937 | Eurich | 73/440 |
| 2,168,353 | 8/1939 | Linebarger | 73/451 |
| 2,282,069 | 5/1942 | Linebarger | 73/454 |
| 2,296,169 | 9/1942 | Linebarger | 73/449 |
| 2,332,807 | 10/1943 | Moore | 73/452 |
| 2,674,119 | 4/1954 | Trainor | 73/441 |
| 2,674,120 | 4/1954 | Trainor | 73/454 |
| 2,766,623 | 10/1956 | De Giers | 73/440 |
| 3,908,467 | 9/1975 | Schwen | 73/440 |
| 3,956,922 | 5/1976 | November | 73/32 A |
| 4,037,481 | 7/1977 | Callahan | 73/454 |

FOREIGN PATENT DOCUMENTS

| | | | |
|---|---|---|---|
| 410935 | 5/1934 | United Kingdom | 73/451 |
| 426097 | 3/1935 | United Kingdom | 73/451 |
| 462051 | 7/1936 | United Kingdom | 73/451 |

OTHER PUBLICATIONS

B. Keramati et al., "Device for Direct Measurement of Fluid Densities", *Review of Scientific Instruments,* vol. 46, No. 11, pp. 1573-1577, Nov. 1975.

*Primary Examiner*—Stephen A. Kreitman
*Attorney, Agent, or Firm*—Fulbright & Jaworski

[57] ABSTRACT

A densimeter for measuring the density of a fluid with a disk-shaped body having an axis with a horizontal component and being rotatably mounted on a shaft along the axis. Two open cavities are provided in the body so that the center of buoyancy of the body is displaced maximally from the axis. The body has a generally homogeneous density and includes a region wherein the density is different from that of the disk. Because of the density anomaly the center of gravity of the body is displaced from both the center of buoyancy and from the axis. The outer perimeter of the body and the cavities are circular so as to encounter minimal drag resistance while rotating in a fluid. When the densimeter is placed in a fluid, the disk will oscillate on the shaft. The density of the fluid is determined from the angular position of the disk on the shaft upon reaching equilibrium.

7 Claims, 19 Drawing Figures

PENDULUM DENSIMETER

CROSS-REFERENCES TO RELATED APPLICATIONS

This application is a continuation-in-part of copending patent application Ser. No. 688,266 filed May 20, 1976 entitled Densimeter, now U.S. Pat. No. 4,136,551.

BACKGROUND OF THE INVENTION

1. Field of the Invention

This invention relates to devices for measuring the specific gravity of a fluid.

2. Description of the Prior Art

Densimeters are well known and have been used for many years to measure the specific gravity of fluids. For measuring the specific gravity of liquid in a battery, hydrometers are used which include a float in a hollow tube. As the fluid is drawn up into the tube the float seeks a level in the fluid proportional to the specific gravity of the fluid. Various types of hydrometers are shown in U.S. Pat. Nos. 1,898,903; 2,674,119; and 2,674,120. A densimeter for measuring the specific gravity of a moving stream of fluid is shown in U.S. Pat. No. 2,332,807. There are many applications in which these devices are not suitable. For example, when the specific gravity of an opaque fluid such as petroleum or milk is needed, the indicator of the device must be such that it can be read without regard to the petroleum or milk or through a foam build-up of each. Also the hydrometer of the U.S. Pat. No. 1,898,903 is not practical with large, deep containers such as tank cars because it would have to be mounted at the top of the car. Consequently, a densimeter is needed that can be used with a wide range of fluids and in hard to reach locations. Another problem is involved with moving fluids. The response of the densimeter must not follow the motion of the fluid. The hydrometer of U.S. Pat. No. 2,674,119 has serrated edges which will interact with the stream of fluid. Also, the device of U.S. Pat. No. 2,332,807 could not be used directly in a moving stream of fluid because its response would correspond to the hydrodynamic forces.

SUMMARY OF INVENTION

The present invention of a pendulum densimeter is used to measure the specific gravity of a fluid whether in motion or not. The densimeter includes one or two members mounted on a shaft so that at least one member is rotatable on the shaft. When the densimeter is placed in a fluid, the member oscillates to an equilibrium position on the shaft. The equilibrium position reached is an indication of the specific gravity of the fluid. The outer contours of the rotatable member are rounded so as to minimize the fluid dynamic effects when rotating in the fluid or in a moving fluid.

Another embodiment of the densimeter includes two rotatable members on the same shaft where one of the members rotates counter to the other for more accurate measurements in gases or to amplify the measurement taken.

Another feature is that the oscillating member includes two circular holes on one side of a diameter for maximally displacing the center of buoyancy from the axis as well as minimizing fluid dynamic effects.

Other features of the invention pointed out in the claims can best be illustrated by the following description of preferred embodiments of the invention.

DESCRIPTION OF THE DRAWINGS

For a more detailed description of a preferred embodiment of the invention, reference will now be made to the accompanying drawings wherein.

DESCRIPTION OF THE PREFERRED EMBODIMENT

Figure 1:
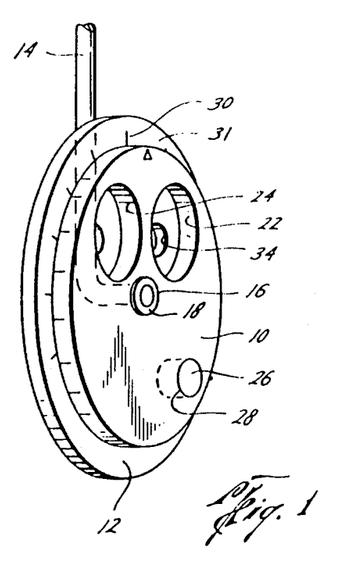
FIG. 1 is an isometric view of one embodiment of the invention.
Figure 2:
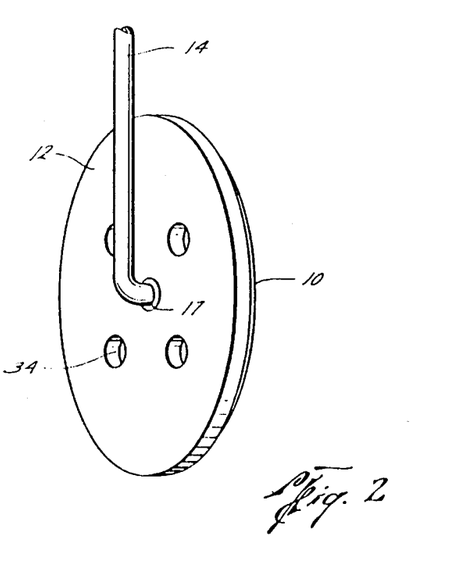
FIG. 2 is another isometric view of the embodiment of FIG. 1.

Referring now to FIGS. 1 and 2, there is shown a first disk 10 rotatably mounted on shaft 14 through bore 16 that extends through disk 10. A second disk 12 may be mounted on shaft 14 through bore 17. The disks 10, 12 are preferably circular and of a homogeneous material. The disks 10, 12 are retained on shaft 14 by means of retaining washer 18 that is fixedly attached to shaft 14. Hollow regions 22, 24 are formed in disk 10. The hollow regions 22, 24 are shown as two circular bores, positioned on one side of a diameter of disk 10. The hollow regions 22, 24 cause the center of buoyancy of the disk to be displaced from the suspension point at bore 16. Another requisite is to make the hollow region on the inside or flat surface of disk 10 so as not to interfere with the fluid dynamic characteristics of disk 10. Indentations or recesses with steep entry angles such as a perpendicular bore offer little fluid resistance and are preferred.

Disk 10 also has a mass insert 26 that is placed in bore 28. Insert 26 may be a circular disk, however, any size or shape may be used so that the center of gravity of the disk 10 with insert 26 is displaced from both bore 16 and the center of buoyancy. The insert may be either liquid-filled or solid. Insert 26 is typically flush with the surface of disk 10 so as to minimize its effect on the fluid dynamic characteristics of the disk 10.

Disk 12 which is also mounted on shaft 14 has a larger diameter than disk 10. The larger diameter of disk 12 allows a density scale 30 to be placed thereon. Disk 10 is provided with an indication marker 31 that cooperates with scale 30 to indicate the specific gravity of the fluid. As shown in FIG. 2, disk 12 has bores 34 therethrough to allow fluid collecting between disk 10 and disk 12 to pass through. Since the primary function of disk 12 is to provide a scale 30 thereon, disk 12 need not be a circular disk and could be of almost any shape that would not interfere with the rotation of disk 10.

In operation, the densimeter of FIG. 1 is placed in the fluid to be measured so that bore 16 has a horizontal component to its orientation. It may be extended into the fluid by shaft 14. If the location of the fluid requires an extremely long shaft, a chain or cable might be more suitable than a shaft. When the device encounters the fluid, the effect of the displacement of the center of buoyancy from the center of gravity of disk 10 and the displacement of both centers from bore 16 causes disk 10 to oscillate on shaft 14 until equilibrium is reached, i.e. when the downward gravity force balances the upward buoyant force. The equilibrium angular position of disk 10 on shaft 14 indicates the density of the fluid. Since disk 12 does not rotate, the marker 31 will indicate the density on scale 30.

It is generally not necessary to lock disk 10 to disk 12 because the bores 34 in disk 12 allow the fluid between the disks to pass through upon removal from the fluid. If care is taken upon removal, the surface tension of the fluid will cause disk 10 to hold its angular position. Also if the opposing surfaces of disks 10, 12 are rough, the interaction of the two rough surfaces will cause the disk 10 to hold its position. If the fluid is excessively turbulent it might be necessary to mechanically lock disk 10 as will be described hereinafter. An advantage of this densimeter when used with a turbulent fluid is that it is in the shape of a flat circular disk which has very little hydrodynamic interference either with a moving fluid or oscillating in a fluid.

Figure 3:
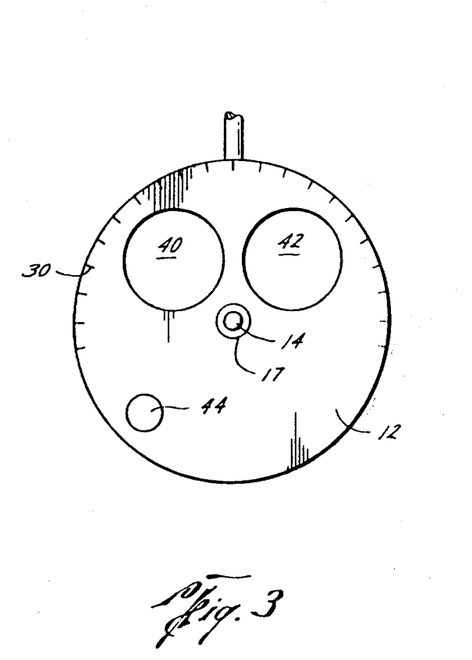
FIG. 3 is a plan view of another embodiment of the invention.

Referring now to FIG. 3, there is shown another embodiment of disk 12 that is rotatably mounted on shaft 14 through bore 17 as in FIGS. 1, 2. Disk 10 is not shown for clarity. Disk 12 is made of the same homogeneous material as disk 10 and includes hollow regions 40, 42 and insert 44 which are similar in size, shape, location, and density to those of disk 10. When placed on shaft 14, disk 12 is oriented so that its insert 44 and hollow regions 40, 42 cause it to rotate in the opposite direction to disk 10. This is accomplished by mounted disk 12 on shaft 14 so that insert 44 is in a quadrant of disk 12 adjacent the quadrant of insert 26 in disk 10. This can be seen by comparing FIGS. 1 and 3.

In this embodiment the densimeter is placed in the fluid to be measured and both disks 10 and 12 rotate to an equilibrium position on shaft 14. Disk 12 is mounted on shaft 14 so as to rotate in the opposite direction to disk 10. Thus, a much more accurate scale 30 may be used on disk 12 since the same fluid density will cause twice the total angular rotation on shaft 14. If hollow regions 40, 42 are bored completely through disk 12, the bores 34 as shown in FIG. 1 will not be needed to drain the fluid between the disks so that the disks 10, 12 lock together by surface tension of the fluid and by roughening their opposing surfaces. Again if care is exercised this densimeter may be used without a locking mechanism.

Figure 4:
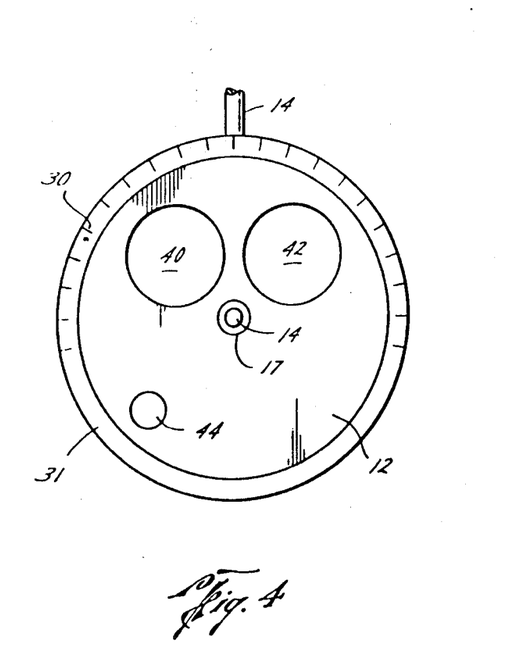
FIG. 4 is a plan view of another embodiment of the invention.

Referring now to FIG. 4 there is shown another embodiment of disk 12 wherein scale 30 is placed on ring 31. Ring 31 is attached to disk 12, and attachment may be accomplished by screws or bolts or by cooling disk 12 until ring 31 fits therearound. The addition of ring 31 of density different from disk 12 provides the feature of changing the density of disk 12. If the device were to fall completely into the fluid being measured, ring 31 could act as a buoy to float the densimeter on the surface for easy retrieval. A similar ring 31 might be mounted around disk 10 so that disk 10 will also float. On the other hand, by adding a ring 31 of sufficient weight to disk 10, the locking of the angular position of disk 10 will be augmented if the device is removed from the liquid so that a heavy disk 10 bears against disk 12.

Figure 5:
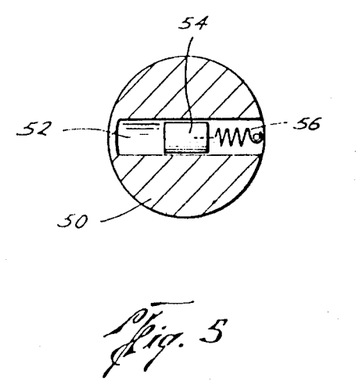
FIG. 5 is an enlarged fragmentary sectional view of another embodiment of the insert of FIG. 1.

Referring now to FIG. 5, there is shown an enlarged view of an insert 50 which is similar to the insert 26 of disk 10. Insert 50 is shown as a flat disk although any size or shape may be used. Insert 50 has a bore 52 therein in which another insert 54 is carried. Insert 54 is preferably made of metal. A bimetallic strip 56 typically in the form of a helical spring attaches at one end to the insert 50 and at the other end to the metal insert 54.

This embodiment of insert 50 is used to provide for temperature compensation. As the temperature of the fluid may vary, the center of buoyancy of the disk 10 will vary due to counteraction or expansion. Since the coefficient of expansion of the material of disk 10 may differ from that of the fluid being measured, the density measured will be incorrect due to temperature variation. The temperature compensating means of metal insert 54 and bimetallic spring 56 acts to change the center of gravity of disk 10 by moving insert 54 in correlation with change in temperature. This change in the center of gravity affects the rotation of the disks about shaft 14 and thereby compensates for changes in temperature. If the dual rotating disk device of FIG. 3 is used, insert 50 also replaces insert 44 of disk 12.

Another important design factor of insert 50 is the angle of the bore 52 to the vertical. As disks 10, 12 rotate on the shaft, the angle of the bore 52 to the vertical will also change. The pull of gravity on metal insert 54 and bimetallic spring 56 will affect the temperature compensation of spring 56. Consequently, the initial angle of the bore 52 with respect to the vertical must be predetermined for each instrument depending upon the desired density range of each. Insert 50 could, however, be rotatably mounted in disks 10, 12 so that the angle of bore 52 to the vertical will not change upon rotation of disks 10, 12.

Referring again to FIG. 1, the angular displacement of disk 10 on shaft 14 does not vary linearly with density of the surrounding fluid. Telemetry means, hereinafter described, such as linear differential transformers, piezoelectric devices or any other suitable device may be used to transmit a signal corresponding to the angular position of disk 10 on shaft 14 and thus the specific gravity of the surrounding fluid may be monitored. The electronic signal, without providing for linearization, will correspond to the angular position of disk 10 on shaft 14, and nonlinearities of up to 9% for a rotation of 180° may result. If a telemetry receiver expects a linear input, which is desirable, inaccuracies of up to 9% for a rotation of 180° may therefore result.

Figure 6:
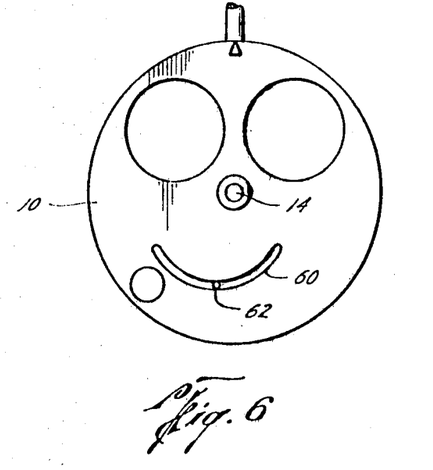
FIG. 6 is a plan view of another embodiment of the invention.

The embodiment of FIG. 6 linearizes such angular nonlinearities. In this embodiment disk 10 is modified to include an arcuate groove 60 in which is disposed a mass 62. Mass 62 may be spherical or cylindrical or any suitable shape to allow it to roll in groove 60. The modified disk 10 is then rotatably mounted to shaft 14 as in FIG. 1 or FIG. 3. Upon rotation of disk 10, mass 62 will roll in groove 60 and the position of mass 62 will vary with the angle of rotation of disk 10. Thus, the center of gravity of disk 10 will vary with rotation. By this manner linearity is possible with rotations of ±150 degrees.

Figure 7:
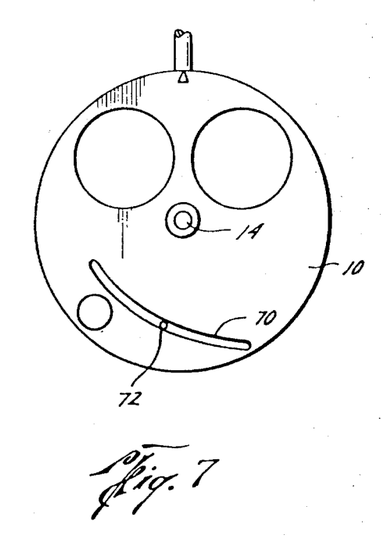
FIG. 7 is a plan view of another embodiment of the invention.

The particular shape of arcuate groove 60 is not limited. FIG. 6 shows a circular arc groove 60; however, FIG. 7 shows a spiral groove 70 that is closer to the axis of suspension of the disk at one end of the groove than at the other. Mass 72 is carried by groove 70 and rolls in groove 70 as disk 10 rotates on shaft 14. The output (position) of disk 10 will be linearized by the change of the center of gravity of disk 10 due to the position of mass 72 in groove 70. The shape of groove 70 will have to be determined for each type model.

Figure 8:
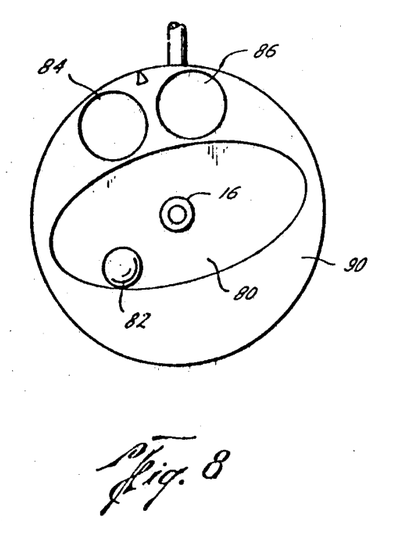
FIG. 8 is a plan view of another embodiment of the invention.

Referring now to FIG. 8 there is shown another embodiment of the linearizing arcuate groove. A cavity 80 in disk 9 having an arcuate inner perimeter surrounds the axis of suspension, i.e., bore 16, and may be filled with a liquid and contain a mass 82 therein which may roll on the perimeter thereof. Hollow regions 84, 86 in disk 90 function as with regions 22, 24 of disk 10 in FIG. 1 to displace the center of buoyancy, however, the insert 26 of disk 10 in FIG. 1 has been replaced by mass 82. The density of the liquid used in the cavity and the coefficient of expansion thereof should preferably match that of the disk 10 material. The mass 82 may be of any suitable mass that will roll on the perimeter of the cavity, typically a ball bearing or a cylindrical disk.

Instead of using a mass 62, 72, 82, the embodiments of the linearity devices of FIGS. 6-8, respectively, might have groove or cavity 60, 70 or 80, respectively, filled with a liquid of density different from that of the disk 10 or 90, such that an air bubble is trapped within the groove or cavity 60, 70, or 80. As disk 10 or 90 rotates, the air bubble will shift due to the downward gravitational force thereby effectively shifting the center of gravity of the fluid in the groove. Thus the center of gravity of disk 10, 90 will be shifted and linearity may be achieved.

Figure 9:
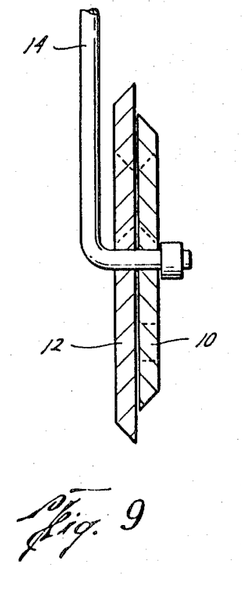
FIG. 9 is a fragmentary vertical sectional view of another embodiment of the invention.

Referring now to FIG. 9, there is shown another embodiment of the densimeters of FIGS. 1-8 that may be used with liquids such as drilling mud having solids which tend to settle out and adhere to any devices encountered thereby. The disks 10, 12 are similar to disks 10, 12 of FIG. 1 except there are no right angle corners for mud or solids to collect thereon. All surfaces are at steep angles of inclination to the vertical including, for example, the perimeters of hollow regions 22, 24 of disk 10 and the holes 34 of disk 12 of FIG. 1. Since drilling mud generally undergoes irregular motion, the inertial qualities of the disk 10 are designed so that the effects of the motion of the mud on the rotation of disks 10, 12 will be minimized.

Figure 10:
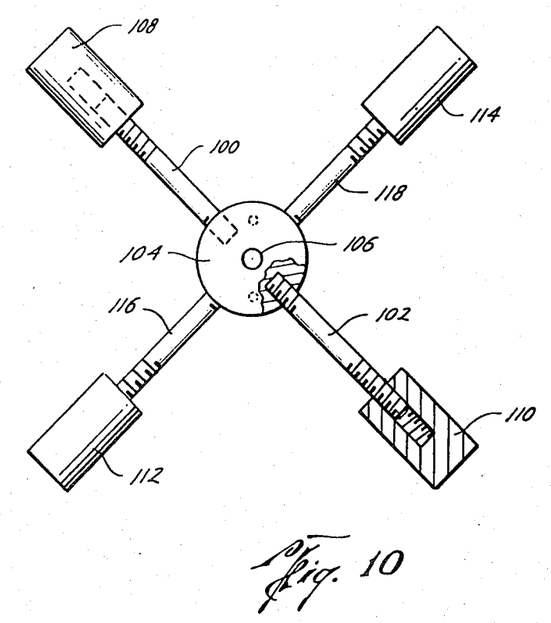
FIG. 10 is a fragmentary sectional view of another embodiment of the invention.
Figure 11:
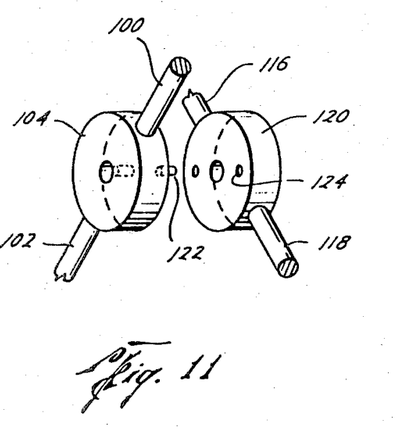
FIG. 11 is an enlarged isometric view of the embodiment of FIG. 9.

Referring now to FIG. 10, there is shown another embodiment of a densimeter. Spokes 100, 102 are connected to bearing 104. Bearing 104 is rotatably mounted to shaft 106. Threadedly connected to each outer end of spokes 100, 102 are masses 108, 110, respectively. Masses 108, 110 and spokes 100, 102 combine to provide a first configuration that has its center of gravity and the center of buoyancy displaced from each other and from the center of suspension at bearing 104. A second configuration similar to the first is composed of masses 112, 114 threadedly connected to the end of spokes 116, 118, respectively. As shown in FIGS. 10 and 11, spokes 116, 118 are then connected to bearing 120 that is also rotatably mounted to shaft 106. Bearings 104 and 120 are locked together through splines 122 on bearing 104 and grooves 124 on bearing 120. It is desirable that the first set and second set are similar in size and design characteristics. An advantage of a four-spoke device is that the first set of spokes, masses, and bearings can be made identical to the second set. Since each bearing interlocks with the other, the first set of spokes and masses can be calibrated separately from the second set. Then when both sets have been adjusted, which may be accomplished by changing the position of the masses on the threads of their respective spokes, they are interlocked through the bearings onto shaft 106.

This embodiment of the densimeter of FIGS. 10-11 is useful to measure the density of gases. Since gases have very low densities, the densimeters of FIGS. 1-8 would not be responsive enough for accurate measurement because of manufacturing difficulties due to accuracy considerations and friction generated during rotation of the disks 10, 12. A four-spoke densimeter, as shown in FIG. 10, can be much more responsive and sensitive to gas densities. By varying the length of the spokes and the masses, this four-spoke device can also be made responsive to a wide range of gas densities.

Figure 12:
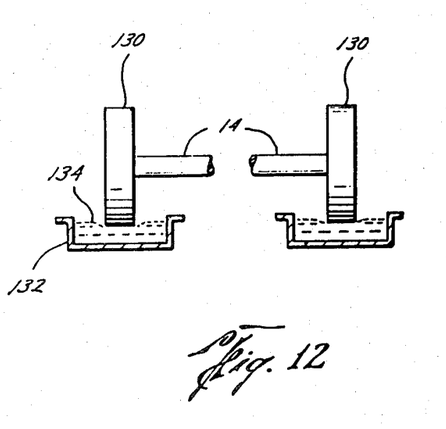
FIG. 12 is a plan view of a floating bearing embodiment.

For measuring gas density, the bearings 104, 120 may, however, have too much friction when rotating on a shaft such as shaft 14 to be responsive to a general range of gas densities. FIG. 12 shows a substitute bearing system for bearings 104, 120 wherein shaft 14 is mounted on a fixed bearing 130 that is placed in a container 132 of mercury 134. Bearings 130 float on the mercury 134 so that there is very little friction. The material of the container 132 should be of a material that will form an amalgam on the inside edge with the mercury 134 in the container 132 so that a conventional meniscus will form and the mercury 134 does not stick to the inside of container 132. This floating bearing is sufficiently low in friction loss to be useful in gas density measurement, however, other types of low friction bearings such as air bearings or magnetic bearings may be used.

Figure 13:
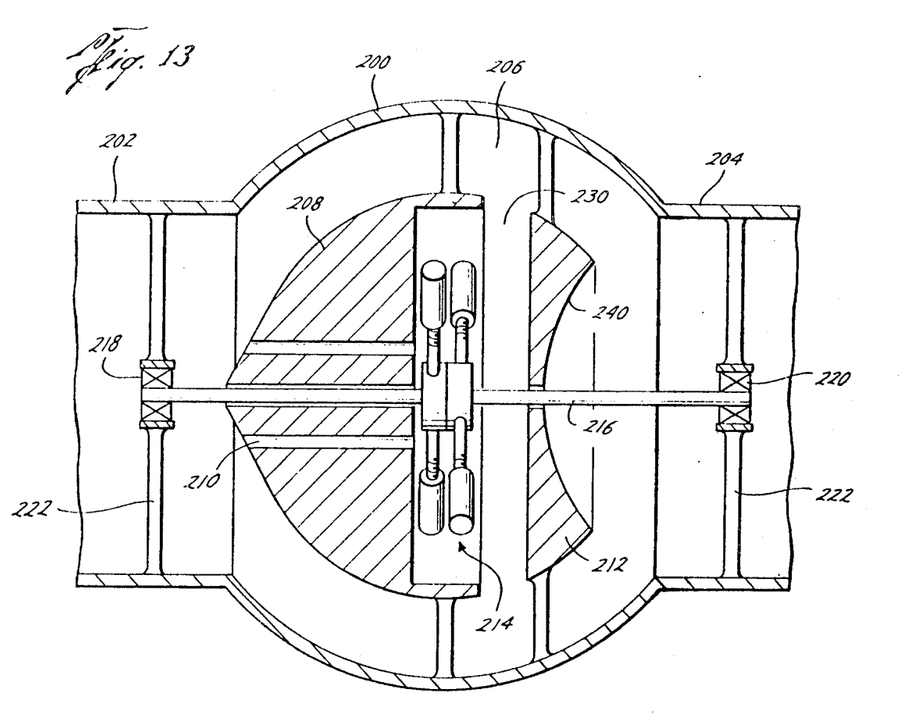
FIG. 13 is a fragmentary vertical sectional view of another embodiment of the invention.

Referring now to FIG. 13, there is shown an embodiment of the densimeter of FIG. 10 that is designed for use with flowing gases. Housing 200 is joined at one end to inlet conduit 202 and at the other end to outlet conduit 204. Housing 200 provides a plenum chamber 206 in which is disposed a front dome-like shield 208 centrally located in the chamber 206. Orifices 210 in front shield 208 allow gas flowing from inlet conduit 202 to outlet conduit 204 to pass through shield 208. A back shield 212 is also disposed in the plenum chamber 206 downstream of the front shield 208. Between the front and back shields 208, 212, a chamber 230 is formed, and the four spoke device 214 of FIG. 10 is rotatably mounted therein on shaft 216. Shaft 216 is coaxially disposed in the housing 200 and is mounted on bearings 218, 220 to struts 222 which are connected to housing 200. Shaft 216 extends through both front shield 208 and back shield 212. An electronic readout device may then be used to monitor the angular position of the shaft 216.

In this embodiment, the gas sample flows from inlet conduit 202 into plenum chamber 206. Most of the gas flows around front shield 208 and back shield 212 and into outlet conduit 204. Orifices 210 in front shield 208 allow the gas to enter chamber 230 between front shield 208 and back shield 212. Upon encountering the gas in chamber 230, the four spoke device 214 will rotate with shaft 216 to an equilibrium position so that the buoyant forces and gravitational forces are equalized. The angular equilibrium position of shaft 216 thus will correspond to the specific gravity of the gas. An electronic readout device then will monitor the shaft 216 position to a recording station. The back shield 212 is arcuately contoured at 240 so as to shield the four-spoke device 214 from turbulence resulting from the gas flowing around front shield 208.

The embodiment of FIG. 13 is a highly sensitive device for making gas density measurements in a flowing gas stream. By making the measurements in chamber 230 the gas will be substantially at rest and the fluid dynamic effects on the four-spoke device 214 will be negligible.

Figure 14:
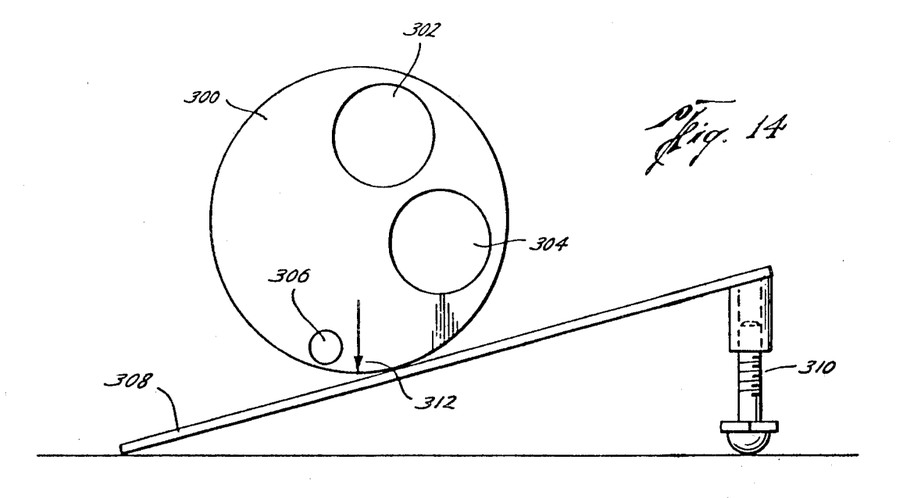
FIG. 14 is a plan view of another embodiment of the invention.

Referring now to FIG. 14, there is shown another embodiment of a densimeter for measuring gas densities in which accurate measurements are necessary and friction losses are important. A disk device such as disk 10 shown in FIG. 1, consisting of circular disk 300, hollow regions 302, 304, and heterogeneous insert 306, is disposed on platform 308. Platform 308, which may be straight or curved, is tilted by means of screws 310. Disk 300 has an indication marker 312 pointing downwardly.

Typically in this embodiment, the disk 300 and platform 308 are surrounded by the fluid. The platform 308 is then tilted so that the disk 300 will roll thereon until the marker 312 points downwardly. By calibrating the angle of tilt for a known gas, the angle of tilt for a gas sample will correspond to the density of the gas. This device alleviates some of the problems with friction because the only friction involved is rolling friction between disk 200 and platform 208, and rolling friction is small compared to the sliding friction encountered with bearings.

Figure 15:
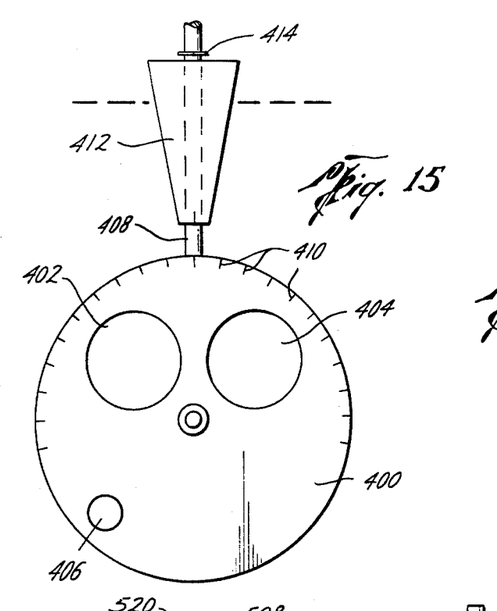
FIG. 15 is an elevational view of one means for locking one embodiment after a reading has been taken.
Figure 16:
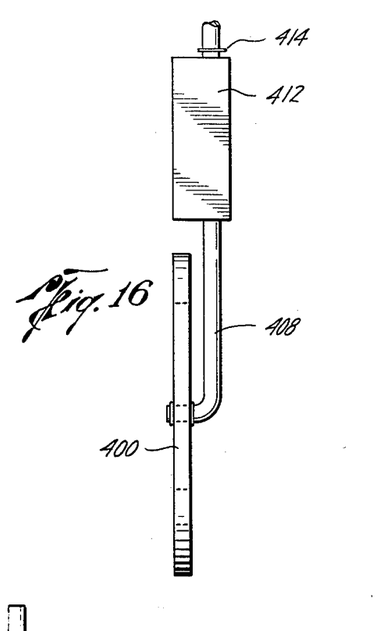
FIG. 16 is a side view of the apparatus of FIG. 15.

Referring now to FIGS. 15 and 16, there is shown another embodiment of a densimeter, a single disk similar to the disk 10 shown in FIG. 2 consisting of a circular disk 400, circular hollow regions 402 and 404 which are positioned on one side of a diameter of the disk 400 for shifting the center of buoyancy away from the axis of the disk 400 for obtaining maximum buoyancy while at the same time minimizing dynamic resistance. A heterogeneous insert 406 is provided in the disk 400 for positioning the center of gravity of the disk 400 away from both the axis of the disk 400 and the center of buoyancy of the disk 400. The disk 400 is supported on its axis such as by a support such as shaft 408 whereby the disk 400 may oscillate when it is placed in a liquid to be measured until it reaches its equilibrium. While the disk 400 may suitably measure specific gravity of a fluid which can be measured and indicated by markings 410 as they are positioned relative to the shaft 408, it may be desirable in some instances to provide a locking means to lock the disk 400 in position so that it can be retrieved from the fluid and its rotational position observed for measurement purposes. One suitable locking means may be a float 412 which is slidably positioned on the shaft 408. Thus, when the disk 400 is positioned in a fluid, the float 412 will move up the shaft 408 and out of contact with the disk 400. Once the disk 400 has reached its equilibrium position which is a measurement of the specific gravity of the fluid in which it is immersed, the support 408 is raised and the float 412 will slide down the upper portion of the shaft 408 to rest against the outer periphery of the disk 400 to prevent its rotation as it is removed from the fluid. Preferably, the interconnection between the float 12 and the shaft 408 is non-circular to prevent rotation of the float 412 relative to the shaft 408 which could also rotate the disk 400 causing erroneous readings. If desired, a stop 414 can be placed on the shaft 408 to limit the distance of travel of the float 412 away from the disk 400.

Figure 17:
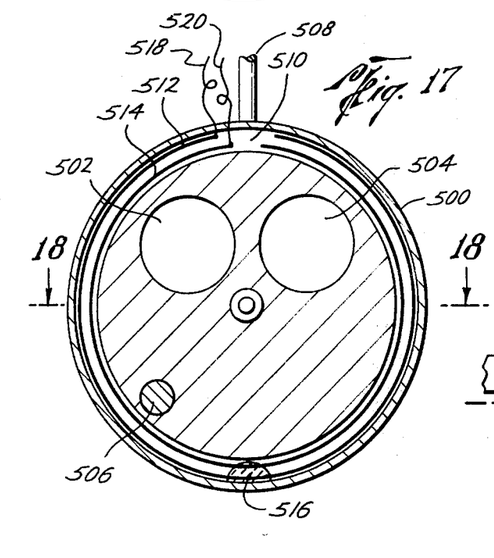
FIG. 17 is an elevational view of one embodiment of the present invention with one form of telemetering means.
Figure 18:
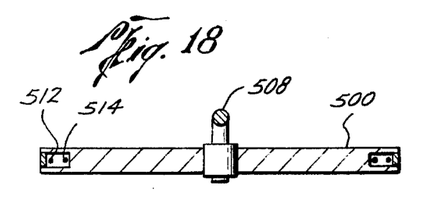
FIG. 18 is a cross-sectional view taken along the line 18—18 of FIG. 17.

Referring now to FIGS. 17 and 18, a single disk embodiment is shown utilizing telemetering for measuring the rotational position of the disk and thus the specific gravity of the fluid in which it is immersed. The disk 500 is a circular disk including circular hollow regions 502 and 504 and a heterogeneous insert 506 and is rotatable about its axis on a support 508. For telemetering a circular groove 510 is positioned around the disk 500 and contains two parallel resistance conductors 512 and 514. Also positioned in the groove 510 is a movable electrical conductor such as mercury blob 516 which maintains its position in the bottom part of the groove 510 as the disk 500 moves. The conductor 516 will short out between the parallel conductors 512 and 514 and a measurement of the resistance by leads 518 and 520 would be a measurement of the rotational position of the disk 500 and thus of the specific gravity of the fluid. Of course, the leads 518 and 520 should be sufficiently slack so as not to interfere with the rotation of the disk 500 during measurement.

Figure 19:
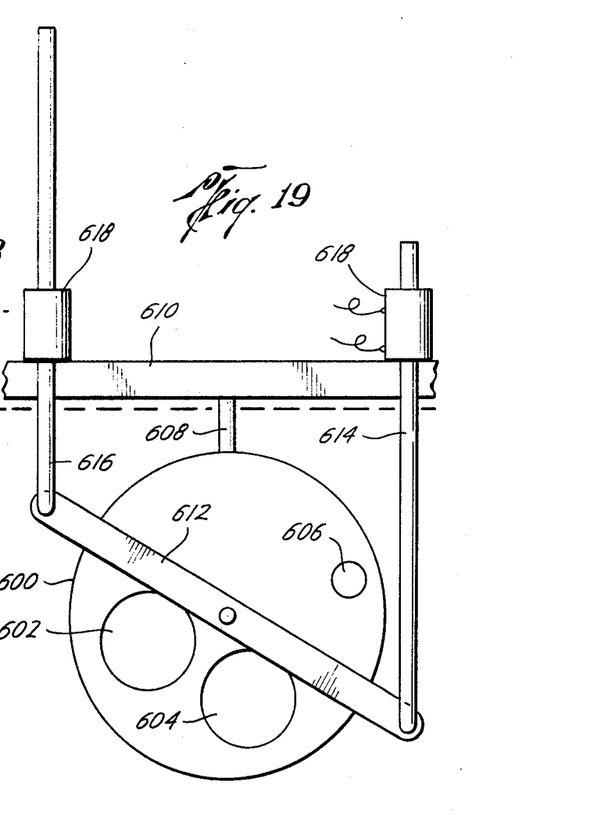
FIG. 19 is an elevational view of one embodiment of the present invention with another form of telemetering means.

Referring now to FIG. 19, another suitable means for telemetering the rotational position of a single disk is shown. The circular disk 600 having circular hollow regions 602 and 604 and a weighted insert 606 is rotatable about its axis from a support 608 which may be suitably supported such as on a float 610. A shaft 612 is secured to and rotates with the disk 600. Pivotally connected to each end of the shaft 612 are identical rods 614 and 616 which extend upwardly. A suitable measuring means such as a linear differential transformer measures the vertical position of the rod 614 and thus of the rotational position of the disk 600. If desired, the other rod 616 may pass through an electromagnetic vibrator 618 for applying vibrations to the rods 616, the shaft 612 and the disk 600 which is advantageous in some instances when the disk 600 is attempting to measure specific gravity of highly viscous fluids such as drilling muds.

The above are merely exemplary of the possible changes or variations of the invention. Many varying and different embodiments may be made within the scope of the inventive concept herein taught and many modifications may be made in the embodiment herein detailed in accordance with the descriptive requirements of the law. It is understood, therefore, that the details herein are to be interpretated as illustrative and not limitative.

What is claimed as inventive is:

1. A device for measuring the specific gravity of a fluid comprising,
   a circular disk having an axis and a bore therethrough and along said axis,
   a shaft extending through said bore and said disk being rotatably mounted thereon,
   said disk including two circular holes therein with both positioned on one side of a diameter of the disk for displacing the center of buoyancy of the disk from said axis, a material mounted in said disk for displacing the center of gravity of said disk from said center of buoyancy and from said axis, and means for measuring the angular position of said disk relative to said shaft.

2. The apparatus of claim 1 including electrical means for measuring the angular position of said disk.

3. The apparatus of claim 2 wherein the electrical means includes a circular body having first and second circular resistance wires therein and a movable conductive body.

4. The apparatus of claim 2 wherein the electrical means includes a shaft connected to the disk and a transducer connected to the shaft for measuring the position of the shaft.

5. The apparatus of claim 2 wherein the electrical means includes a shaft extending through the axis of the disk, a rod connected to each end of the shaft, a transducer connected to one of the rods, and a vibrator connected to the other rod.

6. The apparatus of claim 1 including locking means for locking the disk in position after a measurement.

7. The apparatus of claim 6 wherein the locking means includes a float slidably connected to the shaft and positioned above the disk for disengaging the disk when the disk is inserted in a fluid, but which engages the disk when the disk is removed from the fluid.

* * * * *